(12) United States Patent
Tsai et al.

(10) Patent No.: US 11,998,894 B2
(45) Date of Patent: Jun. 4, 2024

(54) COMPOSITE SOLID BASE CATALYST, MANUFACTURING METHOD THEREOF AND MANUFACTURING METHOD OF GLYCIDOL

(71) Applicants: NATIONAL TSING HUA UNIVERSITY, Hsinchu (TW); Chang Chun Plastics Co., Ltd., Taipei (TW); Chang Chun Petrochemical Co., LTD., Taipei (TW); DAIREN CHEMICAL CORP., Taipei (TW)

(72) Inventors: De-Hao Tsai, Hsinchu (TW); Yung-Tin Pan, Hsinchu (TW); Che-Ming Yang, Hsinchu (TW); Ching-Yuan Chang, Hsinchu (TW); Ding-Huei Tsai, Hsinchu (TW); Chien-Fu Huang, Taipei (TW); Yi-Ta Tsai, Taipei (TW)

(73) Assignees: NATIONAL TSING HUA UNIVERSITY, Hsinchu (TW); Chang Chun Plastics Co., Ltd., Taipei (TW); Chang Chun Petrochemical Co., LTD., Taipei (TW); DAIREN CHEMICAL CORP., Taipei (TW)

( * ) Notice: Subject to any disclaimer, the term of this patent is extended or adjusted under 35 U.S.C. 154(b) by 0 days.

(21) Appl. No.: 17/839,618

(22) Filed: Jun. 14, 2022

(65) Prior Publication Data
US 2023/0234033 A1   Jul. 27, 2023

(30) Foreign Application Priority Data
Jan. 21, 2022 (TW) .................................. 111102679

(51) Int. Cl.
*B01J 21/04* (2006.01)
*B01J 21/02* (2006.01)
(Continued)

(52) U.S. Cl.
CPC ............... *B01J 23/04* (2013.01); *B01J 21/02* (2013.01); *B01J 35/50* (2024.01); *B01J 37/0209* (2013.01); *B01J 37/08* (2013.01); *C07D 301/02* (2013.01)

(58) Field of Classification Search
CPC ... B01J 21/04; B01J 21/10; B01J 23/02; B01J 35/026; B01J 37/0209; B01J 37/08; C07D 301/02
(Continued)

(56) References Cited

U.S. PATENT DOCUMENTS 7,045,481 B1 * 5/2006 Parasher ............... C01B 15/026
502/118
8,349,761 B2 * 1/2013 Xia ...................... B01J 37/0215
977/773
(Continued)

FOREIGN PATENT DOCUMENTS

CN        102744053 A    10/2014
CN        109876790 A     6/2019

OTHER PUBLICATIONS

Hoang et al., "Cu—ZnO@Al2O3 hybrid nanoparticle with enhanced activity for catalytic CO2 conversion to methanol," Advanced Powder Technology, (2021), vol. 32, No. 5: 1785-1792.
(Continued)

*Primary Examiner* — Cam N. Nguyen
(74) *Attorney, Agent, or Firm* — McBee Moore & Vanik, IP, LLC

(57) ABSTRACT

A composite solid base catalyst, a manufacturing method thereof and a manufacturing method of glycidol are provided. The composite solid base catalyst includes an aluminum carrier and a plurality of calcium particles. The plurality of calcium particles are supported by the aluminum
(Continued)

carrier. Beta basic sites of the composite solid base catalyst are 0.58 mmol/g-3.89 mmol/g.

21 Claims, 8 Drawing Sheets

(51) Int. Cl.
| | |
|---|---|
| *B01J 21/10* | (2006.01) |
| *B01J 23/02* | (2006.01) |
| *B01J 23/04* | (2006.01) |
| *B01J 35/02* | (2006.01) |
| *B01J 35/50* | (2024.01) |
| *B01J 37/02* | (2006.01) |
| *B01J 37/08* | (2006.01) |
| *C07D 301/02* | (2006.01) |

(58) Field of Classification Search
USPC .............................. 502/332, 341, 355, 415
See application file for complete search history.

(56) References Cited

U.S. PATENT DOCUMENTS

| | | | | |
|---|---|---|---|---|
| 8,356,607 | B2* | 1/2013 | Inoue | A24B 15/287 |
| | | | | 131/365 |
| 9,540,241 | B2* | 1/2017 | Kumar | B01J 37/0018 |
| 9,649,627 | B1* | 5/2017 | Xiao | B01J 37/08 |
| 9,878,305 | B2* | 1/2018 | Hossain | B01J 35/1009 |
| 10,695,749 | B2* | 6/2020 | Xiao | B01J 23/60 |
| 10,875,092 | B2* | 12/2020 | Veerabhadrappa | B01J 35/023 |
| 10,919,026 | B2* | 2/2021 | Xiao | B01J 23/89 |
| 11,351,604 | B2* | 6/2022 | Veerabhadrappa | B01J 37/18 |

OTHER PUBLICATIONS

Milewski et al., "Preparation of Glycidol via Dehydrohalogenation of 3-Chloro-1,2-popanediol Using Bipolar Membrane Electrodialysis," ACS Sustainable Chem. Eng., 2019, vol. 7, pp. 18640-18646.
Pasupulety, "Production of biodiesel from soybean oil on CaO/Al2O3 solid base catalysts," Applied Catalysis A: General, vol. 452, 2013, pp. 189-202.

* cited by examiner

US 11,998,894 B2

COMPOSITE SOLID BASE CATALYST, MANUFACTURING METHOD THEREOF AND MANUFACTURING METHOD OF GLYCIDOL

RELATED APPLICATIONS

This application claims priority to Taiwan Application Serial Number 111102679, filed Jan. 21, 2022, which is herein incorporated by reference.

BACKGROUND

Technical Field

The present disclosure relates to a solid base catalyst and a manufacturing method thereof. More particularly, the present disclosure relates to a composite solid base catalyst for catalyzing the synthesis of glycidol and a manufacturing method thereof.

Description of Related Art

A lot of chemical reactions, such as esterification, transesterification, ring-opening etherification and deacidification cyclization, are used in the petrochemical process to turn the petroleum material into petrochemical products with high value added. The aforementioned chemical reactions can be catalyzed by homogeneous base catalysts. The homogeneous base catalysts can be in contact with the petroleum material evenly to increase the reaction rate. Moreover, the homogeneous base catalysts have the advantages of high activity and high selectivity, so the homogeneous base catalysts are widely used in the petrochemical process.

However, the homogeneous base catalysts are evenly mixed with the reactant and the product, so other purifying steps, such as distillation or extraction, are required to successfully separate the product from the homogeneous base catalysts after the reaction is finished. It is difficult to reuse the separated homogeneous base catalysts. Please note that, the manufacturing cost rises due to the purifying steps, and massive wastewater and energy consumption in the purifying steps becomes a burden to the environment.

In this regard, it has become a pursuit target for vendors to develop a catalyst which is suitable for petrochemical process and able to reduce the negative impacts caused by the purifying steps.

SUMMARY

According to one aspect of the present disclosure, a composite solid base catalyst includes an aluminum carrier and a plurality of calcium particles. The plurality of calcium particles are supported by the aluminum carrier. Beta basic sites of the composite solid base catalyst are 0.58 mmol/g-3.89 mmol/g.

According to one embodiment of another aspect of the present disclosure, a manufacturing method of the composite solid base catalyst of the aforementioned aspect includes the steps as follows. A reactant solution is provided, a titrating step is performed, a ripening step is performed and a calcination step is performed. The reactant solution includes an aluminum ion and a calcium ion. In the titrating step, a potassium hydroxide solution is titrated with the reactant solution, so as to form a stock solution. In the ripening step, the stock solution stands until a catalyst precursor forms. In the calcination step, the catalyst precursor is heated, so as to obtain the composite solid base catalyst.

According to another embodiment of another aspect of the present disclosure, a manufacturing method of the composite solid base catalyst of the aforementioned aspect includes the steps as follows. The aluminum carrier is provided, a reactant solution is provided, an impregnating step is performed and a calcination step is performed. The reactant solution includes a calcium ion. In the impregnating step, the reactant solution is made in contact with the aluminum carrier, so as to obtain a catalyst precursor. In the calcination step, the catalyst precursor is heated, so as to obtain the composite solid base catalyst.

According to one another aspect of the present disclosure, a manufacturing method of glycidol includes steps as follows. The composite solid base catalyst of the aforementioned aspect is provided, and a deacidification step is performed. In the deacidification step, a deacidification of 3-chloropropane-1,2-diol is catalyzed by the composite solid base catalyst, so as to form glycidol.

BRIEF DESCRIPTION OF THE DRAWINGS

The present disclosure can be more fully understood by reading the following detailed description of the embodiment, with reference made to the accompanying drawings as follows.

DETAILED DESCRIPTION

Figure 1:
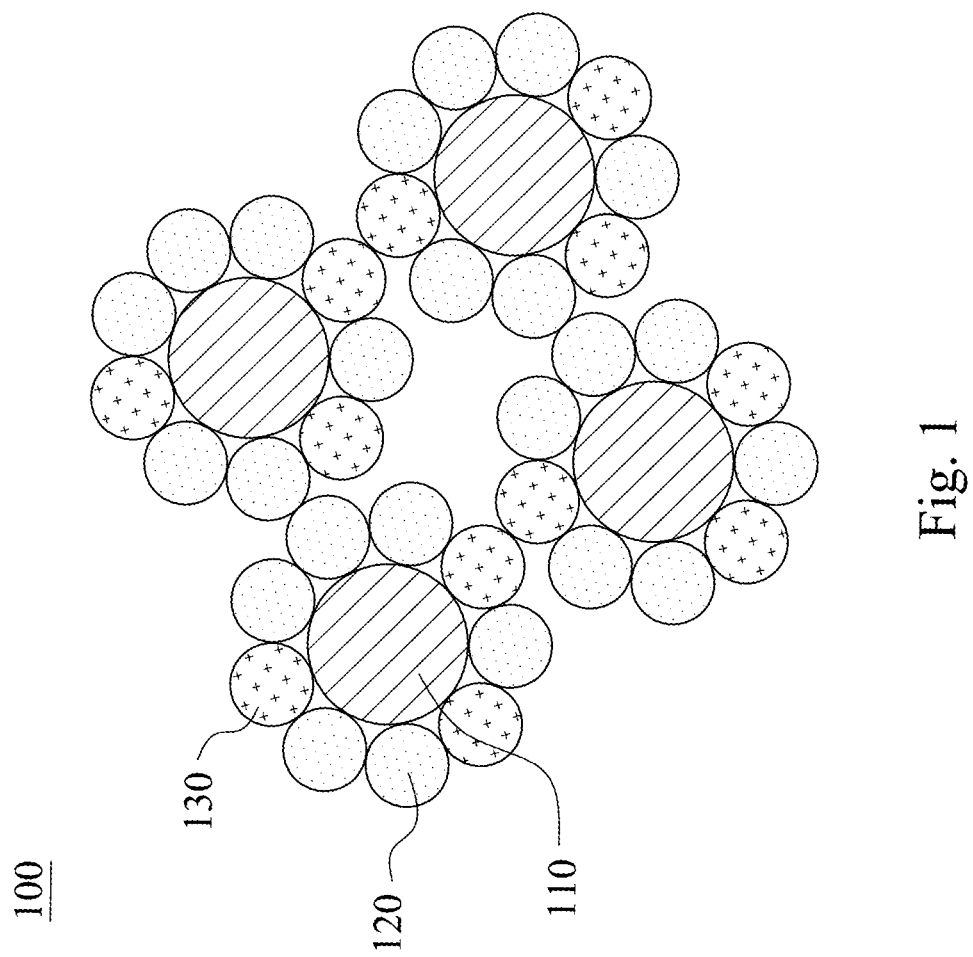
FIG. 1 is a structural schematic view of a composite solid base catalyst according to one aspect of the present disclosure.

The present disclosure will be further exemplified by the following specific embodiments. However, the embodiments can be applied to various inventive concepts and can be embodied in various specific ranges. The specific embodiments are only for the purposes of description, and are not limited to these practical details thereof. Furthermore, in order to simplify the drawings, some conventional structures and elements will be illustrated in the drawings by a simple and schematic way.

Please refer to FIG. 1. FIG. 1 is a structural schematic view of a composite solid base catalyst 100 according to one aspect of the present disclosure. According to one aspect of the present disclosure, the composite solid base catalyst 100 includes an aluminum carrier 110 and a plurality of calcium particles 120.

In detail, the calcium particles 120 are supported by the aluminum carrier 110. Because the materials of the calcium particles 120 are alkaline earth metals, the pH value of the composite solid base catalyst 100 can be controlled for further application. On the other hand, because the calcium particles 120 are supported by the aluminum carrier 110, a concerted reaction happens at an interface of the aluminum carrier 110 and the calcium particles 120, which enhances the reactivity and stability of the composite solid base catalyst 100.

Beta basic sites of the composite solid base catalyst 100 are 0.58 mmol/g-3.89 mmol/g. The beta basic sites are $Ca^{2+}$—$O^{2-}$ basic sites formed by $O^{2-}$ ions adjacent to OH groups on the surface of the calcium particles 120. By adjusting the amount of beta basic sites of the composite solid base catalyst 100, higher conversion can be obtained and the yield of the chemical reaction can be further enhanced.

The aluminum carrier 110 can be an aluminum oxide nanoparticle, and a weight ratio of the aluminum carrier 110 to the composite solid base catalyst 100 can be 15%-80%. Each of the calcium particles 120 can be a calcium oxide nanoparticle, and a weight ratio of the calcium particles 120 to the composite solid base catalyst 100 can be 20%-85%. The selectivity of the composite solid base catalyst 100 will be excellent with suitable element ratio (that is, ratio of calcium to aluminum).

The composite solid base catalyst 100 can further include a plurality of magnesium particles 130, and the magnesium particles 130 can be supported by the aluminum carrier 110. Each of the magnesium particles 130 can be a magnesium oxide nanoparticle, and a weight ratio of the magnesium particles 130 to the composite solid base catalyst 100 can be 12%-18%, which is preferably 13%. The magnesium particles 130 are added as active ingredients of the composite solid base catalyst 100, which is favorable for adjusting the selectivity and conversion of the catalyzed by the composite solid base catalyst 100.

Figure 2:
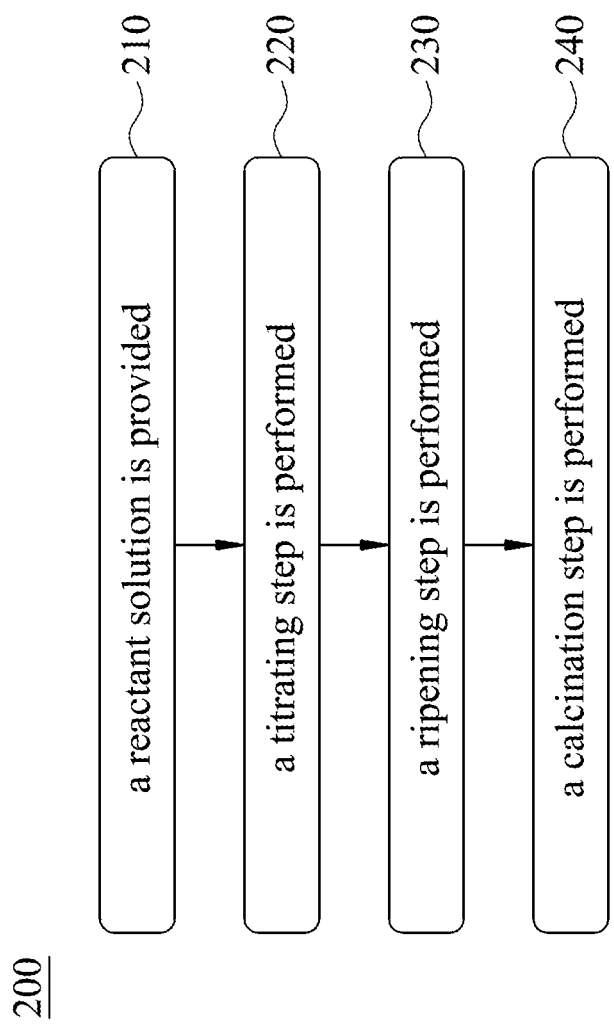
FIG. 2 is a flow chart of a manufacturing method according to one embodiment of another aspect of the present disclosure.

Please refer to FIG. 1 and FIG. 2. FIG. 2 is a flow chart of a manufacturing method 200 according to one embodiment of another aspect of the present disclosure. According to one embodiment of another aspect of the present disclosure, the manufacturing method 200 of the aforementioned composite solid base catalyst 100 includes Step 210, Step 220, Step 230 and Step 240.

In Step 210, a reactant solution is provided. The reactant solution includes an aluminum ion and a calcium ion. The calcium ion can form the calcium particles 120 and be supported by the aluminum carrier 110 which is formed by the aluminum ion. The aluminum ion in the reactant solution can be from aluminum nitrate, and the calcium ion can be from calcium nitrate. A molar ratio of the calcium ion to the aluminum ion in the reactant solution can be 1.5-5.0, so as to ensure that the aluminum ion and calcium ion are enough for the reaction in the following steps.

In Step 220, a titrating step is performed. A potassium hydroxide solution is titrated with the reactant solution, so as to form a stock solution. In the titrating step, the aluminum ion will react with potassium hydroxide to form aluminum salt, and the calcium ion will react with potassium hydroxide to form calcium salt. The aluminum salt and calcium salt will aggregate in the stock solution and become the composite solid base catalyst 100 through the following steps.

In Step 230, a ripening step is performed by making the stock solution stand until a catalyst precursor forms. Furthermore, the stock solution can stand under an environment of 40° C.-80° C. for 8 hours-16 hours. It provides sufficient reaction time for the aluminum ion and calcium ion, which is favorable for enhancing the yield of the composite solid base catalyst 100.

In Step 240, a calcination step is performed to heat the catalyst precursor, so as to obtain the composite solid base catalyst 100. The catalyst precursor can be heated under 400° C.-600° C. for 2 hours-6 hours. Through the calcination step, the aluminum salt in the catalyst precursor will form the aluminum carrier 110, which is composed mainly of aluminum oxide, and the calcium salt will form the calcium particles 120, which is composed mainly of calcium oxide. The impurities in the catalyst precursor can also be removed, and the composite solid base catalyst 100 will have great activity.

Moreover, the reactant solution can further include a magnesium ion, and the magnesium ion can be from magnesium nitrate. A molar ratio of the magnesium ion to the aluminum ion in the reactant solution can be 0.2-1.0. The magnesium ion will also react with potassium hydroxide to form magnesium salt, and then form the magnesium particles 130, which is composed mainly of magnesium oxide, on the aluminum carrier 110 by the calcination step.

Figure 3:
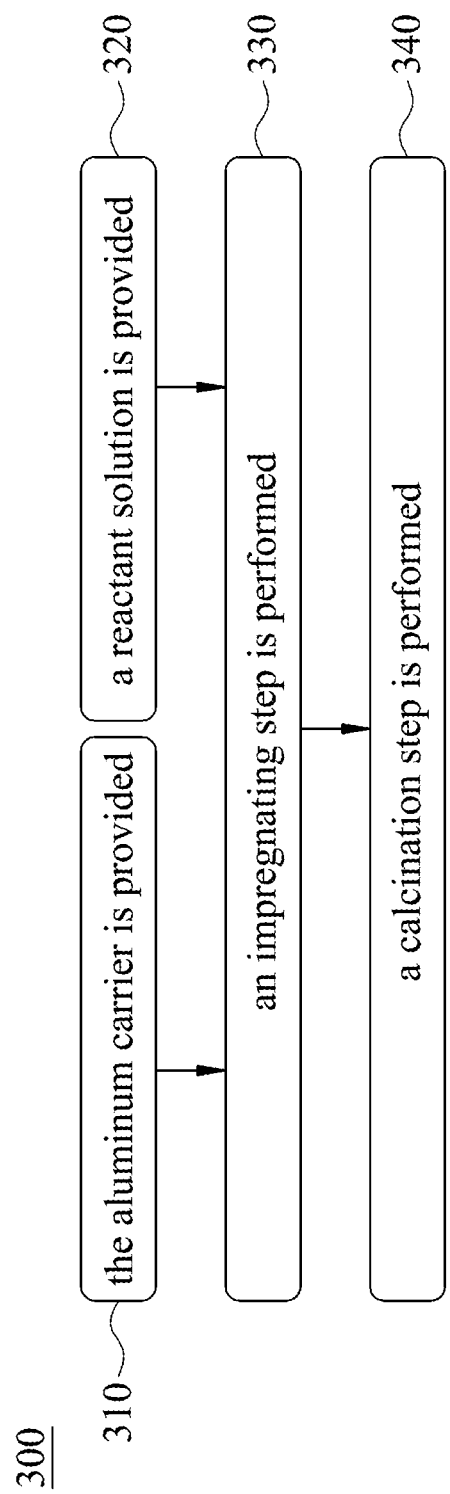
FIG. 3 is a flow chart of a manufacturing method according to another embodiment of another aspect of the present disclosure.

Please refer to FIG. 1 and FIG. 3. FIG. 3 is a flow chart of a manufacturing method 300 according to another embodiment of another aspect of the present disclosure. According to another embodiment of another aspect of the present disclosure, the manufacturing method 300 of the aforementioned composite solid base catalyst 100 includes Step 310, Step 320, Step 330 and Step 340.

In Step 310, the aluminum carrier 110 is provided, and the aluminum carrier 110 can be an aluminum oxide spherical carrier.

In Step 320, a reactant solution is provided, and the reactant solution includes a calcium ion. The calcium ion in the reactant solution can be from calcium nitrate. A molar ratio of the calcium ion in the reactant solution to the aluminum oxide spherical carrier can be 0.5-5.0, or can be 0.48. Through adjusting the ratio of the aluminum oxide spherical carrier and calcium ion, it ensures that the calcium particles 120 supported by the aluminum carrier 110 are enough.

In Step 330, an impregnating step is performed by making the reactant solution in contact with the aluminum carrier 110, so as to obtain a catalyst precursor. In this step, the calcium ion in the reactant solution will attach to the aluminum carrier 110 in a form of calcium salt, and become the calcium particles 120 through the following steps.

In Step 340, a calcination step is performed to heat the catalyst precursor, so as to obtain the composite solid base catalyst 100. The catalyst precursor can be heated under 400° C.-600° C. for 2 hours-6 hours. Through the calcination step, the calcium salt in the catalyst precursor will form the calcium particles 120, which is composed mainly of calcium oxide. The impurities in the catalyst precursor can also be removed, and the composite solid base catalyst 100 will have great activity.

Moreover, the reactant solution can further include a magnesium ion, and the magnesium ion can be from magnesium nitrate. A molar ratio of the aluminum oxide spherical carrier to the magnesium ion in the reactant solution can be 0.5-5.0. The magnesium ion will also form the magnesium particles 130 on the aluminum carrier 110, and the details of the magnesium ion forming the magnesium particles 130 are provided in the aforementioned paragraphs, which will not be given herein.

Figure 4:
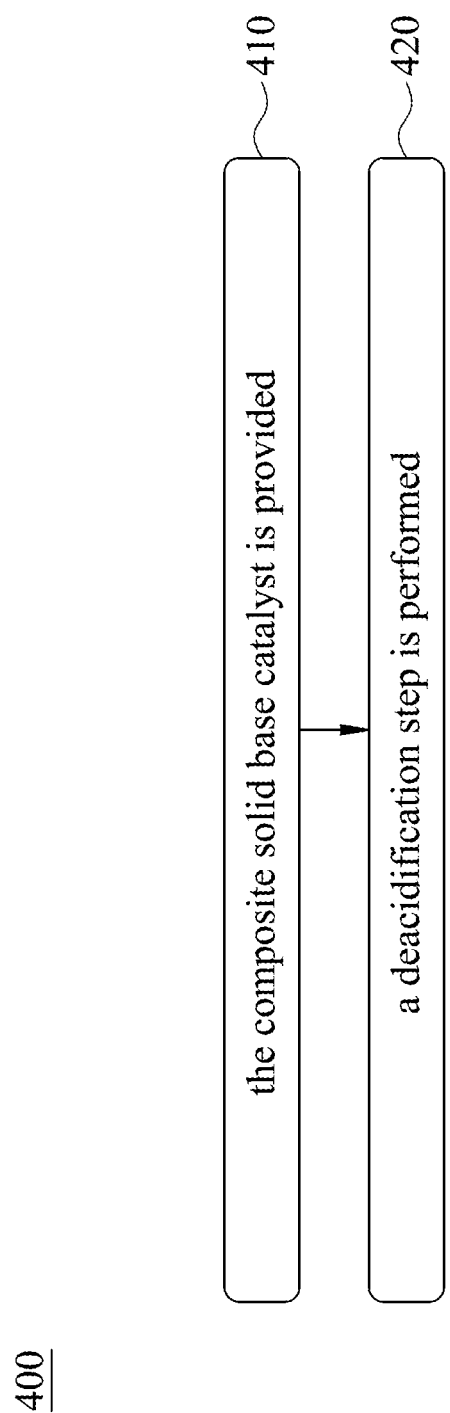
FIG. 4 is a flow chart of a manufacturing method of glycidol according to one another aspect of the present disclosure.

Please refer to FIG. 1 and FIG. 4. FIG. 4 is a flow chart of a manufacturing method of glycidol 400 according to one another aspect of the present disclosure. According to one another aspect of the present disclosure, the manufacturing method of glycidol 400 includes Step 410 and Step 420.

In Step 410, the aforementioned composite solid base catalyst 100 is provided. The composite solid base catalyst 100 has been introduced in the aforementioned paragraphs, and the details will not be given herein.

In Step 420, a deacidification step is performed to catalyze a deacidification of 3-chloropropane-1,2-diol by the composite solid base catalyst 100, so as to form glycidol. The deacidification step can be performed in the reactors such as a batch reactor or a continuous fixed-bed reactor, and the present disclosure is not limited thereto.

Please note that, the deacidification step can be performed under an environment of atmospheric pressure and 30° C.-70° C. Therefore, excessive heat and pressure are not required in the deacidification step to achieve great conversion and selectivity. The possibility of the composite solid base catalyst 100 losing activity due to high temperature and high pressure can be reduced, and the energy consumption and manufacturing cost can be cut down. Furthermore, the deacidification step can be performed under a vacuum environment of 150° C.-160° C. and with a pressure smaller than 20 Torr. The great selectivity can be achieved and the stability of deacidification can be maintained even in the vacuum environment with higher temperature.

In the following paragraphs, the composite solid base catalysts are synthesized by the manufacturing method of the present disclosure. The structures and alkalinities of the composite solid base catalysts are tested and the composite solid base catalysts are applied to the manufacturing of glycidol.

1st Example

The molar ratio of calcium to aluminum of the composite solid base catalyst of the 1st example is 5:1. The composite solid base catalyst of the 1st example is made by the aforementioned manufacturing method 200, and the calcination temperature is 500° C.

2nd Example

The molar ratio of calcium to aluminum of the composite solid base catalyst of the 2nd example is 2:1. The composite solid base catalyst of the 2nd example is made by the aforementioned manufacturing method 200, and the calcination temperature is 500° C.

3rd Example

The molar ratio of calcium to aluminum of the composite solid base catalyst of the 3rd example is 5:1. The composite solid base catalyst of the 3rd example is made by the aforementioned manufacturing method 200, and the calcination temperature is 700° C.

4th Example

The molar ratio of calcium to magnesium to aluminum of the composite solid base catalyst of the 4th example is 3:1:2. The composite solid base catalyst of the 4th example is made by the aforementioned manufacturing method 200, and the calcination temperature is 500° C.

5th Example

The molar ratio of calcium to aluminum of the composite solid base catalyst of the 5th example is 2:1. The aluminum carrier thereof is the aluminum oxide nanoparticle. The composite solid base catalyst of the 5th example is made by the aforementioned manufacturing method 200, and the calcination temperature is 500° C.

6th Example

The molar ratio of calcium to aluminum of the composite solid base catalyst of the 6th example is 0.92:1. The aluminum carrier thereof is the aluminum oxide spherical carrier. The composite solid base catalyst of the 6th example is made by the aforementioned manufacturing method 300, and the calcination temperature is 600° C.

<1st Comparison>

The 1st comparison is a single ingredient of calcium oxide catalyst made by a sol-gel method, and the calcium oxide catalyst is heated at 500° C. in calcination.

<Determination of Morphology of Composite Solid Base Catalyst>

In this experiment, the specific surface area, pore diameters and grain sizes of the calcium particles of the composite solid base catalysts of the 1st example to the 6th example are measured. The results are listed in Table 1 as follows. In Table 1, it can be understood that the structure of the composite solid base catalyst can be modified by adjusting the ratio of elements and the manufacturing conditions in the present disclosure, so as to make the composite solid base catalyst meet the requirements.

TABLE 1

|  | Specific Surface Area ($m^2/g$) | Pore Diameter (nm) | Grain Size of Calcium Particle (nm) |
| --- | --- | --- | --- |
| 1st Example | 7.1 | 28.5 | 35.7 |
| 2nd Example | 5.1 | 22.0 | 28.2 |
| 3rd Example | 6.9 | 31.9 | 40.1 |
| 4th Example | 19.4 | 20.0 | 27.8 |
| 5th Example | 23.4 | 28.9 | 31.3 |
| 6th Example | 57.4 | 11.9 | — |

<Determination of Alkalinity, Conversion and Selectivity>

Figure 5:
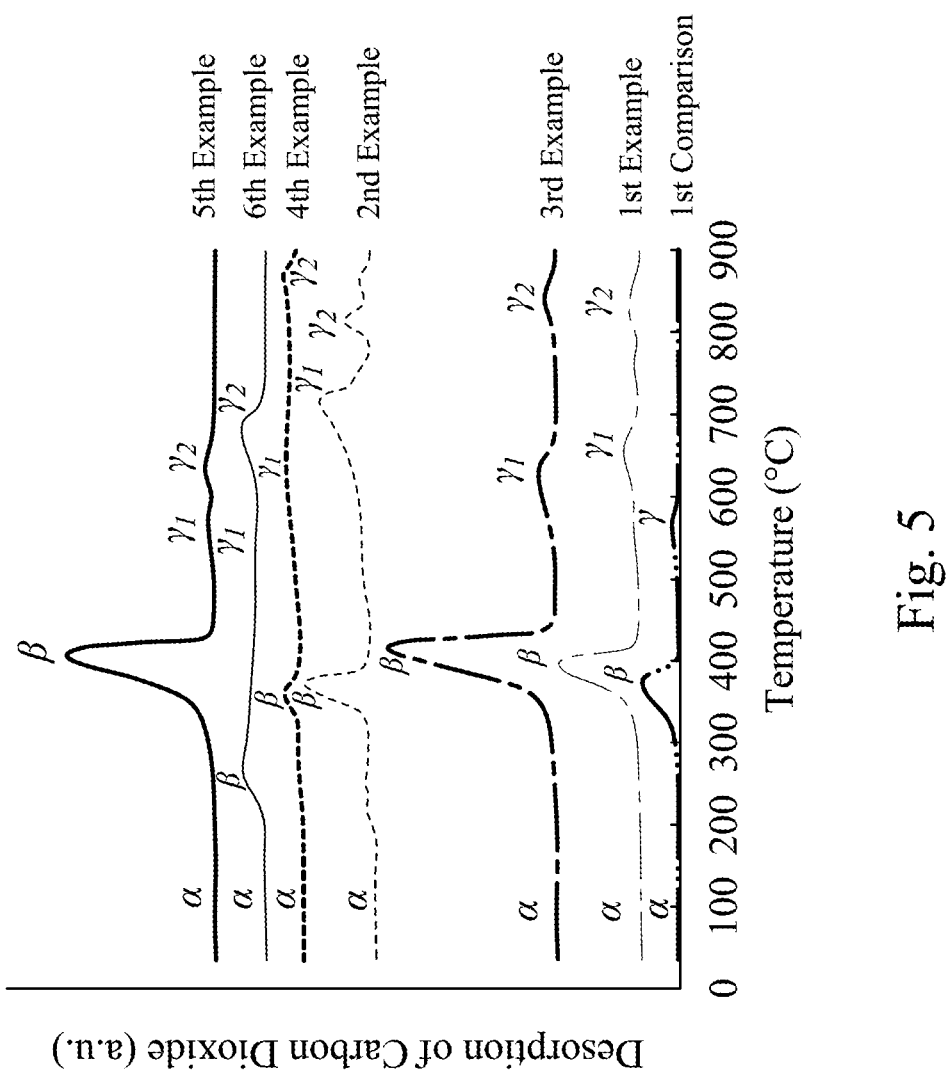
FIG. 5 is a temperature-programmed carbon dioxide desorption diagram of the 1st example to the 6th example of the present disclosure and the 1st comparison.

Please refer to FIG. 5. FIG. 5 is a temperature-programmed carbon dioxide desorption diagram of the 1st example to the 6th example of the present disclosure and the 1st comparison. In this experiment, temperature-programmed carbon dioxide desorption tests of the 1st example to the 6th example and the 1st comparison are performed. The alpha basic site ($\alpha$), beta basic site ($\beta$) and gamma basic sites ($\gamma$, $\gamma_1$, $\gamma_2$) of each catalyst are determined based on the desorption of carbon dioxide.

Figure 6B:
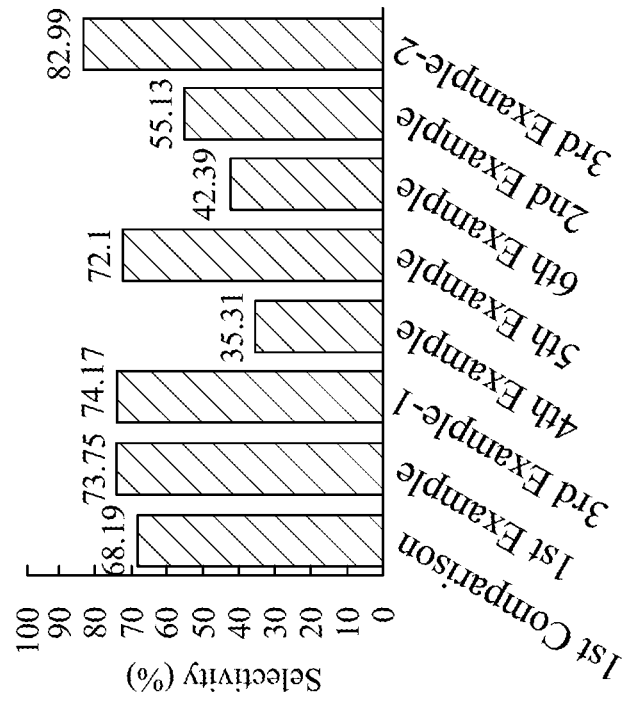
FIG. 6B is a comparative diagram of selectivity of the 1st example to the 6th example of the present disclosure and the 1st comparison.
Figure 6A:
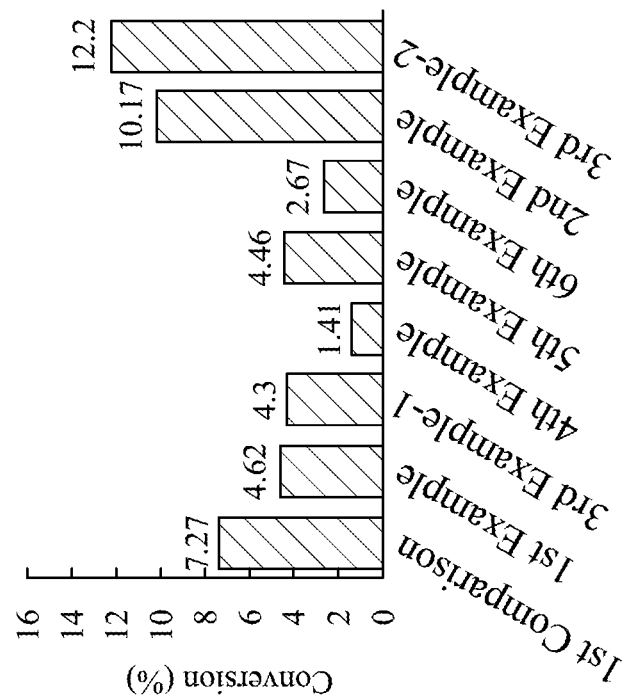
FIG. 6A is a comparative diagram of conversion of the 1st example to the 6th example of the present disclosure and the 1st comparison.

Furthermore, please also refer to FIG. 6A and FIG. 6B. FIG. 6A is a comparative diagram of conversion of the 1st example to the 6th example of the present disclosure and the 1st comparison. FIG. 6B is a comparative diagram of selectivity of the 1st example to the 6th example of the present disclosure and the 1st comparison. The conversion and selectivity of the 1st example to the 6th example and the 1st comparison at the reaction time of 61-90 minutes are determined by the manufacturing method of glycidol of the present disclosure.

Moreover, please refer to FIG. 5, FIG. 6A and FIG. 6B. In FIG. 5, it shows that the composite solid base catalyst of the present disclosure has more beta basic sites. The experiments of "3rd Example-1" and "3rd Example-2" in FIG. 6A and FIG. 6B are performed by using the composite solid base catalyst of the 3rd example, and the usage thereof are 2.5 g and 7.5 g, respectively. In FIG. 6A, the conversion of the 1st example and the 3rd example-1 is smaller than that of the 1st comparison. In FIG. 6B, the selectivity of the 1st example and the 3rd example-1 is larger than that of the 1st comparison. From the abovementioned results, the composite solid base catalyst of the present disclosure has smaller conversion than the single ingredient of calcium oxide catalyst, but has larger selectivity at the reaction time of 61-90 minutes.

Figure 7B:
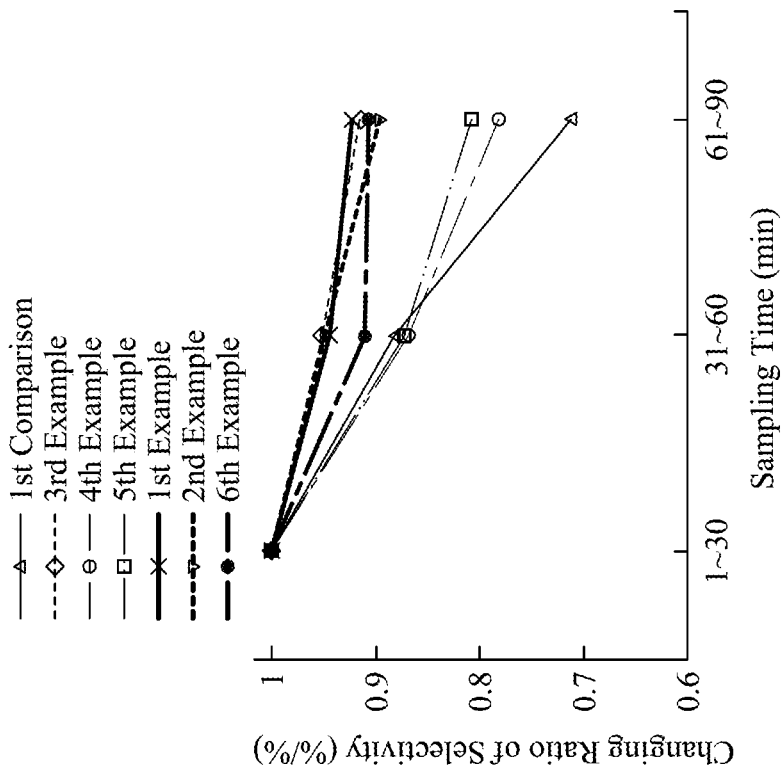
FIG. 7B is a comparative diagram of fractional change of selectivity from its initial value of the 1st example to the 6th example of the present disclosure and the 1st comparison.
Figure 7A:
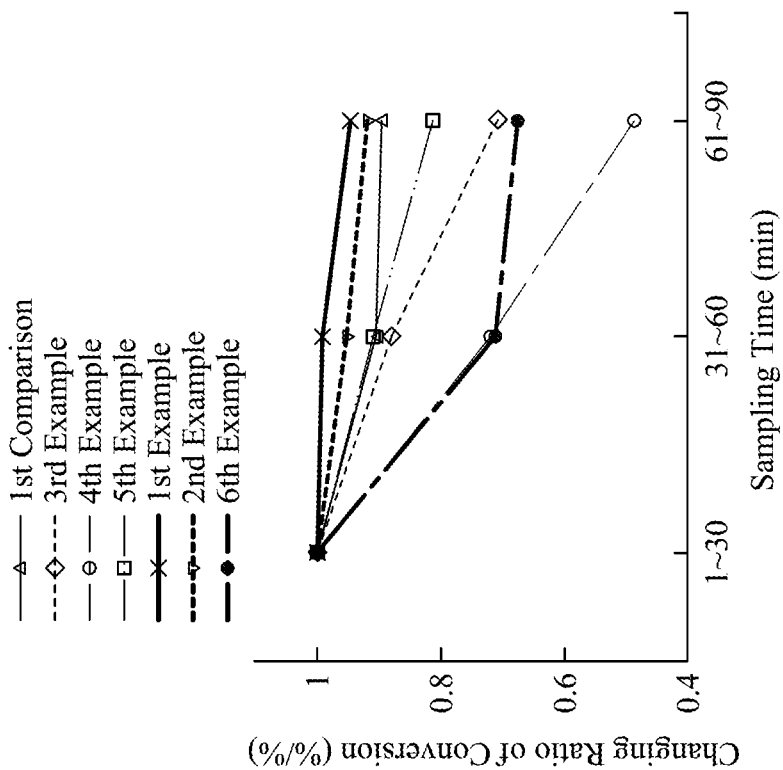
FIG. 7A is a comparative diagram of fractional change of conversion from its initial value of the 1st example to the 6th example of the present disclosure and the 1st comparison.

Furthermore, please refer to FIG. 7A and FIG. 7B. FIG. 7A is a comparative diagram of fractional change of conversion from its initial value of the 1st example to the 6th example of the present disclosure and the 1st comparison. FIG. 7B is a comparative diagram of fractional change of selectivity from its initial value of the 1st example to the 6th example of the present disclosure and the 1st comparison. In FIG. 7A, the decreases of conversion rate of the 1st example and the 2nd example are both smaller than that of the 1st comparison at the reaction time of 61-90 minutes. In FIG. 7B, the decrease of selectivity of the 1st comparison is larger than that of all the examples at the reaction time of 61-90 minutes. From the abovementioned results, the composite solid base catalyst of the present disclosure has better stability than the single ingredient of calcium oxide catalyst.

<Experiment of Manufacturing Glycidol>

Figures 8A, 8B:
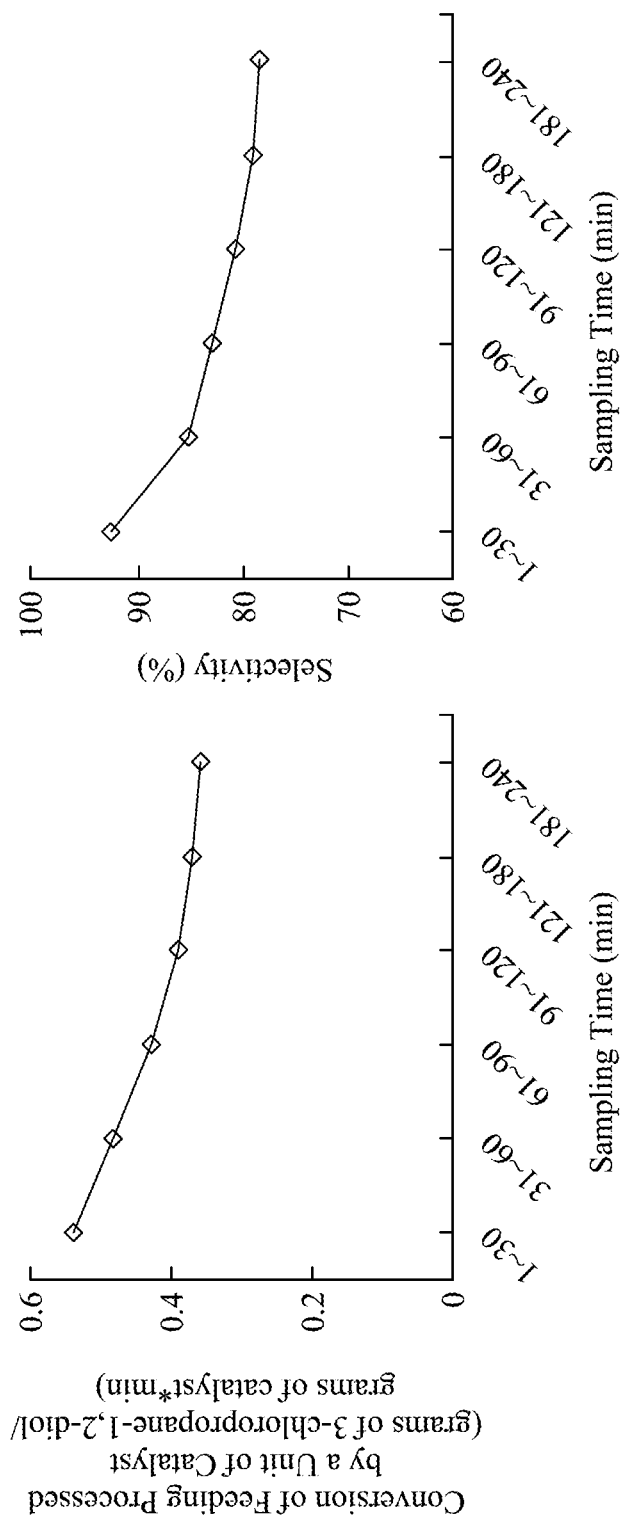
FIG. 8A is a change diagram of conversion as manufacturing glycidol with the composite solid base catalyst of the 3rd example of the present disclosure.
FIG. 8B is a change diagram of selectivity in the manufacturing process of FIG. 8A.

Please refer to FIG. 8A and FIG. 8B. FIG. 8A is a change diagram of conversion as manufacturing glycidol with the composite solid base catalyst of the 3rd example of the present disclosure. FIG. 8B is a change diagram of selectivity in the manufacturing process of FIG. 8A. This experiment is performed by the manufacturing method of glycidol of the present disclosure with the composite solid base catalyst of the 3rd example. In this experiment, the fixed-bed reactor is filled with 7.5 g of the composite solid base catalyst of the 3rd example. 3-chloropropane-1,2-diol and nitrogen are pumped into the reactor with flow rates of 0.2 mL/min and 500 mL/min, respectively. Then, the deacidification is performed under a temperature of 50° C., and the product is analyzed by the gas chromatography to obtain the conversion and selectivity. In FIG. 8A and FIG. 8B, the conversion and selectivity both decrease over time, but the decreasing degree is relatively small, and the conversion and selectivity are still sufficient after reacting for 240 minutes. It shows that the great conversion and selectivity of the composite solid base catalyst of the present disclosure can be maintained after a long reaction.

In this regard, the calcium particles and magnesium particles are supported by the aluminum carrier in the composite solid base catalyst of the present disclosure, and the composite solid base catalyst will go through a heterogeneous catalysis reaction. Therefore, the composite solid base catalyst and the product can be separated easily after the reaction is over. The separated composite solid base catalyst can be reused, which is favorable for reducing the purification cost and purification waste. The goals of environmental friendly and sustainable development can be achieved.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A composite solid base catalyst, comprising:
    an aluminum carrier; and
    a plurality of calcium particles supported by the aluminum carrier;
    wherein beta basic sites of the composite solid base catalyst are 0.58 mmol/g-3.89 mmol/g.

2. The composite solid base catalyst of claim 1, wherein the aluminum carrier is an aluminum oxide nanoparticle, and a weight ratio of the aluminum carrier to the composite solid base catalyst is 15%-80%.

3. The composite solid base catalyst of claim 1, wherein each of the plurality of calcium particles is a calcium oxide nanoparticle, and a weight ratio of the plurality of calcium particles to the composite solid base catalyst is 20%-85%.

4. The composite solid base catalyst of claim 1, further comprising a plurality of magnesium particles supported by the aluminum carrier.

5. The composite solid base catalyst of claim 4, wherein each of the plurality of magnesium particles is a magnesium oxide nanoparticle, and a weight ratio of the plurality of magnesium particles to the composite solid base catalyst is 12%-18%.

6. A manufacturing method of the composite solid base catalyst of claim 1, comprising:
    providing a reactant solution comprising an aluminum ion and a calcium ion;
    performing a titrating step to titrate a potassium hydroxide solution with the reactant solution, so as to form a stock solution;
    performing a ripening step by making the stock solution stand until a catalyst precursor forms; and
    performing a calcination step to heat the catalyst precursor, so as to obtain the composite solid base catalyst.

7. The manufacturing method of claim 6, wherein the aluminum ion in the reactant solution is from aluminum nitrate, and the calcium ion is from calcium nitrate.

8. The manufacturing method of claim 7, wherein a molar ratio of the calcium ion to the aluminum ion in the reactant solution is 1.5-5.0.

9. The manufacturing method of claim 6, wherein the reactant solution further comprises a magnesium ion, and the magnesium ion is from magnesium nitrate.

10. The manufacturing method of claim 9, wherein a molar ratio of the magnesium ion to the aluminum ion in the reactant solution is 0.2-1.0.

11. The manufacturing method of claim 6, wherein in the ripening step, the stock solution stands under an environment of 40° C.-80° C. for 8 hours-16 hours.

12. The manufacturing method of claim 6, wherein in the calcination step, the catalyst precursor is heated under 400° C.-600° C. for 2 hours-6 hours.

13. A manufacturing method of the composite solid base catalyst of claim 1, comprising:
providing the aluminum carrier;
providing a reactant solution comprising a calcium ion;
performing an impregnating step by making the reactant solution in contact with the aluminum carrier, so as to obtain a catalyst precursor; and
performing a calcination step to heat the catalyst precursor, so as to obtain the composite solid base catalyst.

14. The manufacturing method of claim 13, wherein the aluminum carrier is an aluminum oxide spherical carrier, and the calcium ion in the reactant solution is from calcium nitrate.

15. The manufacturing method of claim 14, wherein a molar ratio of the calcium ion in the reactant solution to the aluminum oxide spherical carrier is 0.5-5.0.

16. The manufacturing method of claim 14, wherein the reactant solution further comprises a magnesium ion, and the magnesium ion is from magnesium nitrate.

17. The manufacturing method of claim 16, wherein a molar ratio of the aluminum oxide spherical carrier to the magnesium ion in the reactant solution is 0.5-5.0.

18. The manufacturing method of claim 13, wherein in the calcination step, the catalyst precursor is heated under 400° C.-600° C. for 2 hours-6 hours.

19. A manufacturing method of glycidol, comprising:
providing the composite solid base catalyst of claim 1; and
performing a deacidification step to catalyze a deacidification of 3-chloropropane-1,2-diol by the composite solid base catalyst, so as to form glycidol.

20. The manufacturing method of glycidol of claim 19, wherein the deacidification step is performed under an environment of atmospheric pressure and 30° C.-70° C.

21. The manufacturing method of glycidol of claim 19, wherein the deacidification step is performed under a vacuum environment of 150° C.-160° C. and with a pressure smaller than 20 Torr.

* * * * *